United States Patent [19]

Ohmatoi et al.

[11] 4,287,257
[45] Sep. 1, 1981

[54] PHOSPHORS FOR COLOR TELEVISIONS

[75] Inventors: Susumu Ohmatoi, Fujisawa; Hitoshi Tanaka, Ninomiya; Seiji Murakami, Minami-ashigara, all of Japan

[73] Assignee: Kasei Optonix, Ltd., Tokyo, Japan

[21] Appl. No.: 76,430

[22] Filed: Sep. 17, 1979

[30] Foreign Application Priority Data

Sep. 18, 1978 [JP] Japan ................................. 53/14365

[51] Int. Cl.³ ............................................ C09K 11/10
[52] U.S. Cl. ...................................... 428/403; 427/64; 427/68; 252/301.6 R; 252/301.6 S
[58] Field of Search .................. 252/301.6 R, 301.6 S; 427/64, 68, 215

[56] References Cited

U.S. PATENT DOCUMENTS 2,136,871  11/1938  Wakenhut ...................... 252/301.6 S
2,971,859  2/1961  Siswelos ............................ 427/215

Primary Examiner—Sam Silverberg
Attorney, Agent, or Firm—Gerald J. Ferguson, Jr.; Joseph J. Baker

[57] ABSTRACT

A phosphor for color television surface-treated with zinc hydroxide so that zinc hydroxide attaches thereto in an amount below 0.7 part by weight per 100 parts by weight of the phosphor.

Phosphor slurries for production of phosphor screens prepared from the phosphor have improved light-exposure sensitivity at the formation of and produced from these slurries phosphor screens showing less color mixing.

13 Claims, 5 Drawing Figures

PHOSPHORS FOR COLOR TELEVISIONS

BACKGROUND OF THE INVENTION

1. Field of the Invention

This invention relates to phosphors for color televisions. More particularly, the invention relates to phosphors for color televisions which phosphors are surface-treated for improving the light-exposure sensitivity of phosphor slurries prepared therefrom for formation of phosphor screens.

2. Description of the Prior Art

As is well known, phosphor screens for color television cathode ray (picture) tubes are composed of blue, green, and red emitting phosphor dots or stripes of blue, green, and red emitting phosphor components disposed regularly on a face plate. The phosphor screens for color television picture tubes are prepared by a photoprinting method. That is, a first light emitting phosphor component is dispersed in a solution of a light sensitive resin such as, for example, an aqueous solution of polyvinyl alcohol activated with a dichromate, to provide a phosphor slurry. The phosphor slurry obtained is applied over the whole surface of a face plate by an appropriate coating method such as by rotary coating, etc. (slurry coating), and then the coated layer is irradiated by energy rays or actinic rays such as ultraviolet rays, etc., in conformity with a desired pattern, whereby the resin is hardened and insolubilized at the portions irradiated by the energy rays (light exposure). Thereafter, the resin at the non-irradiated portions (unhardened resin portions) is dissolved away by a solvent, etc. (development) to form dots or stripes composed of the first light emitting phosphor component. Then, by successively repeating slurry coating, exposure and development in the same manner as described above using second and third light emitting phosphor components, dots or stripes composed of the second and third light emitting phosphor components are formed on the face plate. In this case, as a matter of course, the energy ray irradiation must be so controlled that the dots or stripes composed of each of the first, second, and third light emitting phosphor components are repeatedly and regularly disposed on the face plate without being overlapped with each other. Then, the fluorescent screen containing the resin component thus prepared is fired at a proper temperature to decompose and volatilize the resin component, whereby a desired phosphor screen is obtained.

For making phosphor screens for color television picture tubes by a photoprinting method using the above-mentioned phosphor slurries, the following requirements must be met.

1. The phosphor screen must have sufficient thickness and be composed of densely arranged minute dots or stripes of phosphor components;

2. The dots or stripes of phosphor components must be formed in the desired shape at desired positions on a face plate;

3. The light emitting phosphors must not intermix with each other, i.e., color mixing must not occur;

4. The light exposure sensitivity of phosphor slurries must be high and the phosphor slurries have to be easy to work with.

Hitherto, various investigations have been made on the compositions, preparation methods, etc., of phosphor slurries as well as the surface treatment of phosphors (blue, green and red emitting phosphor components) for color television with the aim of satisfying the above-mentioned requirements and the presently used phosphor slurries do in fact satisfy these requirements to some extent. However, from a commercial viewpoint phosphor screens having even higher quality are constantly sought after and hence it has been desired to meet the above requirements more completely.

SUMMARY OF THE INVENTION

One object of this invention is, therefore, to provide surface-treated phosphors for color televisions, which more fully satisfy the above-mentioned requirements, in particular the requirements 3 and 4.

In other words, one object of this invention is to provide surface-treated phosphors for color televisions capable of forming phosphor screens having less color mixing.

Another object of this invention is to provide surface-treated phosphors for color televisions which give phosphor slurries having improved light exposure sensitivity.

It has been discovered that the above-mentioned objects of this invention can be attained by treating phosphors for color televisions with zinc hydroxide so as to attach a proper amount of zinc hydroxide to the surfaces of the phosphors. That is, according to this invention, there is provided a phosphor comprising a phosphor for color television and zinc hydroxide attached to the phosphor for color television, the amount of said zinc hydroxide being less than 0.7 part by weight per 100 parts by weight of the phosphor for color television.

It is also known that the dispersibility of the phosphors for color television in phosphor slurries can be improved by attaching silicon dioxide or a phosphate of magnesium, zinc, calcium, aluminum, etc., to the phosphors, the substance which improves the dispersibility of phosphors for color television being referred to as a "dispersing agent hereinafter" in this specification). Improvement of dispersibility in such manner for the purpose of obtaining phosphor screens having desired properties can be used in combination with the surface treatment of this invention. That is, the dispersing agent may be used in the treatment together with zinc hydroxide. Thus, according to another embodiment of this invention, there is further provided a phosphor comprising a phosphor for color television and zinc hydroxide and a dispersing agent attached to the phosphor for color television, the amount of said zinc hydroxide being less than 0.7 part by weight per 100 parts by weight of the phosphor for color television.

When phosphor screens for color television picture tubes are prepared using the phosphors of this invention, phosphor screens having greatly reduced color mixing are obtained. Also, the phosphor slurries prepared using the phosphors of this invention have a high light exposure sensitivity and hence the period of ultraviolet irradiation (light exposure period) for hardening can be shortened and, moreover, the working efficiency can be increased.

DESCRIPTION OF THE PREFERRED EMBODIMENTS

Figure 1:
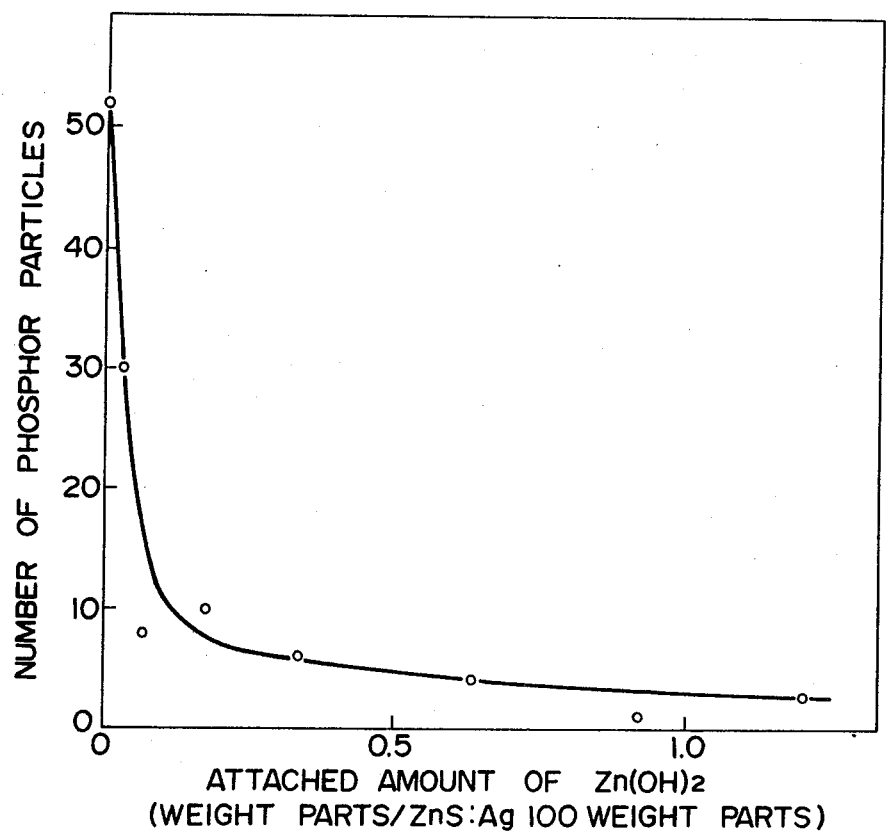
FIG. 1 is a graph showing the relation between the amount of $Zn(OH)_2$ in a $Zn(OH)_2$-attached ZnS:Ag phosphor (including the case that the attached amount is 0)

The invention will now be explained in detail.

The phosphors of this invention are prepared as follows.

A phosphor for color television is first placed in pure water and sufficiently suspended therein. Then, a proper amount of an aqueous solution containing a zinc ion is added to the suspension and thereafter the pH of the suspension containing the zinc ion is adjusted to 7.5–11 by adding an alkali to the suspension to precipitate zinc hydroxide $[Zn(OH)_2]$. The fine particles of $Zn(OH)_2$ thus precipitated attach to the surface of the phosphor. The suspension is allowed to stand to precipitate the phosphor having the fine particles of $Zn(OH)_2$ attached thereto and thereafter the supernatant is removed by decantation. After removing the residual ions by several washings with water, the residue is dehydrated and dried. After drying, the mass of phosphor is passed through a sieve to obtain the desired particulate phosphor.

As the aqueous solution containing a zinc ion, an aqueous solution of a water soluble zinc compound such as, for example, zinc sulfate ($ZnSO_4$), zinc acetate ($Zn(CH_3COO)_2$), zinc nitrate ($Zn(NO_3)_2$), zinc halide ($ZnX_2$ wherein X is a halogen other than fluorine), etc., is used. As the alkali for adjusting the pH of the aqueous solution, an aqueous solution of sodium hydroxide (NaOH), potassium hydroxide (KOH), ammonium hydroxide ($NH_4OH$), etc., is used. When $NH_4OH$ is used, care must be taken so that the pH value of the solution does not go over 10 since excessive addition of ammonium hydroxide causes a soluble ammine complex ion to prevent the deposition of $Zn(OH)_2$.

Drying is performed at temperatures below 250° C., preferably below 200° C. If drying is performed at temperatures higher than 250° C., the $Zn(OH)_2$ attached to the phosphor is wholly converted to ZnO and hence the phosphor of this invention is not obtained. When drying is performed at 200°–250° C., a part of the $Zn(OH)_2$ is converted to ZnO (the ratio of conversion to ZnO becomes higher as the temperature is higher) but the existence of the ZnO thus formed has no adverse influence on the properties of the phosphor. When drying is performed at temperatures below 200° C., the conversion to ZnO scarcely occurs and the $Zn(OH)_2$ remains almost in entirely as it is.

The amount of $Zn(OH)_2$ attached to the phosphor for color television must be larger than 0 part by weight and less than 0.7 part by weight per 100 parts by weight of the phosphor for color television. As the amount of $Zn(OH)_2$ becomes larger than 0.7 part by weight, the dispersibility of the phosphor obtained becomes gradually poorer and when phosphor screens are prepared using phosphors having poor dispersibility, the color mixing becomes severe in proportion to the degradation in dispersibility. A more preferred amount of $Zn(OH)_2$ attached to the phosphor for color television is from 0.01 to 0.5 part by weight per 100 parts by weight of the phosphor. For determining the amount of $Zn(OH)_2$ attached to the phosphor, the use of concentrated aqueous ammonia is convenient. Concentrated aqueous ammonia does not react with a phosphor for color television which is mainly a sulfide or an oxide or with ZnO formed in case of employing a high drying temperature but selectively reacts with $Zn(OH)_2$ to form a soluble ammine complex ion. Consequently, by treating the phosphor prepared according to this invention with concentrated aqueous ammonia to dissolve the $Zn(OH)_2$ as an ammine complex ion and then by separating and quantitatively analyzing the zinc ion, the amount of $Zn(OH)_2$ attached to the phosphor can be determined.

In addition, when a dispersing agent is used together with $Zn(OH)_2$ in the production of the phosphor of this invention, the dispersing agent may be first attached to the phosphor for color television by a conventional method and then $Zn(OH)_2$ may be attached to the phosphor by the above-described method or the dispersing agent may be attached to the phosphor after $Zn(OH)_2$ has been attached thereto. As the dispersing agent used in this case, there can be mentioned silicon dioxide ($SiO_2$) and ortho- meta- or pyro phosphates or magnesium, zinc, calcium, aluminum, etc., ($Mg_3(PO_4)_2$, $Zn_3(PO_4)_2$, $Ca_3(PO_4)_2$, $AlPO_4$, $Mg(PO_3)_2$, $Zn(PO_3)_2$, $Zn(PO_3)_2$, $Ca(PO_3)_2$, $Al(PO_3)_3$, $Mg_2P_2O_7$, $Zn_2P_2O_7$, $Ca_2P_2O_7$, etc.) but $SiO_2$ is particularly preferred. The dispersing agent is attached to the phosphor for color television in the conventional manner. For example, when $SiO_2$ is used as the dispersing agent, the phosphor is first suspended in an aqueous solution of water glass and then an aqueous solution of zinc sulfate, aluminum sulfate, or the like is added to the suspension to deposit the fine particles of $SiO_2$ and then the fine particles of $SiO_2$ are adsorbed on the surface of the phosphor.

The phosphors for color television used in this invention include all the phosphors which can be used as blue, green or red emitting phosphor components for color television picture tubes. The phosphor for color television may be a single phosphor or may be a mixed phosphor such as a green emitting phosphor component composed of a mixture of a copper and aluminum activated zinc sulfide phosphor (ZnS:Cu,Al) and a gold and aluminum activated zinc sulfide phosphor (ZnS:Au,Al). (Such a mixed phosphor is recently seen increased practical use.) Also, for phosphor screens for high contrast color television cathode ray tubes, so-called pigment attached phosphors, i.e., phosphors the surfaces of which have been covered by pigment particles have recently been used and the pigment-attached phosphors may be used as the phosphors for color television in this invention. Therefore, the term "phosphors for color television" in the specification of this invention means any of the single phosphors, the mixed phosphors, and the pigment-attached phosphors as described above.

Particularly preferred phosphors for color television from a practical viewpoint are as follows: as blue emitting phosphors, there can be mentioned a silver activated zinc sulfide phosphor (ZnS:Ag), a silver and aluminum activated zinc sulfide phosphor (ZnS:Ag,Al), a cobalt aluminate blue pigment particle attached ZnS:Ag phosphor, a cobalt aluminate blue pigment particle attached ZnS:Ag,Al phosphor, etc.; as green emitting phosphors, there can be mentioned a mixed phosphor of a ZnS:Cu,Al phosphor and a ZnS:Au,Al phosphor, a ZnS:Cu,Al phosphor, a gold, copper and aluminum activated zinc sulfide phosphor (ZnS:Au,Cu,Al), a copper and aluminum activated zinc-cadmium sulfide phosphor [(Zn,Cd)S:Cu,Al], etc.; and as red emitting phosphors, there can be mentioned a europium activated yttrium oxisulfide phosphor ($Y_2O_2S$:Eu), a europium activated yttrium oxide phosphor ($Y_2O_3$:Eu), a red oxide red pigment particle attached $Y_2O_2S$:Eu phosphor, a red oxide red pigment particle attached $Y_2O_3$:Eu phosphor, a cadmium sulfoselenide red pigment particle attached $Y_2O_2S$:Eu phosphor, a cadmium sulfoselenide red pigment particle attached $Y_2O_3$:Eu phosphor, etc.

The merits of this invention will now be explained with a ZnS:Ag blue emitting phosphor component taken as an illustration.

There are two kinds of color mixing among the light emitting phosphor components in phosphor screens for color television picture tubes. In one case, when a first light emitting phosphor component or a second light emitting phosphor component is slurry-coated, exposed, and developed to form the dots or stripes of the phosphor component on a face plate, the phosphor component remains at positions at which the dots or stripes of another light emitting phosphor component will be formed later, which results in color mixing. Such a residue of phosphor is called "haze". In the other case, when a second or third light emitting phosphor component or a third light emitting phosphor component is slurry-coated, exposed, and developed to form the dots or stripes of the phosphor component, the phosphor component attaches to the dots or stripes of another light emitting phosphor component already formed and remains there. Such color mixing is called "cross contamination". The occurrence of haze depends on the properties of the phosphor slurries, while the occurrence of cross contamination depends upon the properties of the phosphor slurries used and the properties of the dots or stripes already formed.

When the phosphors of this invention are used, the occurrence of color mixing by haze and cross contamination are effectively prevented.

FIG. 1 is a graph showing the relation between the amount of $Zn(OH)_2$ of a $Zn(OH)_2$ attached ZnS:Ag phosphor (including the case that the attached amount is 0). The graph shown in FIG. 1 was obtained as follows. Seven kinds of $Zn(OH)_2$ attached ZnS:Ag phosphors each having a different amount of $Zn(OH)_2$ were prepared using a ZnS:Ag phosphor having attached thereto 0.15 part by weight of $SiO_2$ per 100 parts by weight of the ZnS:Ag phosphor. The 7 kinds of $Zn(OH)_2$ attached ZnS:Ag phosphors and a $Zn(OH)_2$ free ZnS:Ag phosphor (having attached thereto 0.15 part by weight of $SiO_2$) were used as test samples. These the 8 kinds of phosphor samples were also used for obtaining FIGS. 2-4 described below. Then, using each of the phosphor samples, stripes were formed on a face plate as follows.

First, a phosphor slurry was prepared using an aqueous polyvinyl alcohol solution containing conventionally used ammonium bichromate and one of the phosphor samples. Then, each of the phosphor slurries thus obtained was coated on a face plate of a 16 inch picture tube by rotary coating and dried. Thereafter, the coated surface was exposed in stripes through a shadow mask to ultraviolet rays from a high pressure mercury lamp and developed by warm water to form stripes of the phosphor. This manner of forming the stripes was also employed in the case of obtaining the graphs of FIGS. 2-4.

A part of the face plate having stripes formed thereon as described above was projected on a screen under 100 X magnification by means of a magnifying projection microscope and the number of phosphor particles remaining on the unexposed portion, that is, on a 20 mm $\times$ 20 mm area on the screen of the portion between adjacent stripes (a 0.2 mm $\times$ 0.2 mm area on the face plate) was counted. In each of the phosphor samples, the number of remaining particles of phosphor was counted at two portions and the mean value was plotted against the amount of $Zn(OH)_2$ of each phosphor sample (weight part per 100 parts by weight of the ZnS:Ag phosphor). In this way the graph of FIG. 1 was obtained.

As is clear from FIG. 1, the formation of haze decreases as the attached amount of $Zn(OH)_2$ increases. In particular, decreases remarkably with the haze the increase in the amount of attached $Zn(OH)_2$ until the amount of $Zn(OH)_2$ becomes 0.5 part by weight at which point the haze becomes about 1/10 that when the amount of $Zn(OH)_2$ is 0.

Figure 2A:
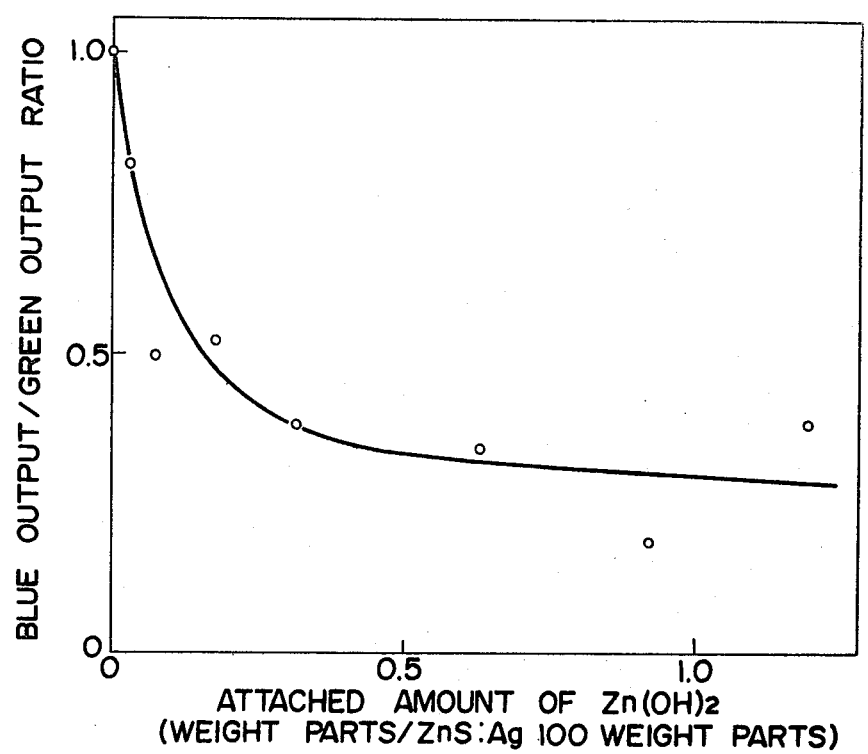
FIG. 2A is a graph showing the relation between the amount of $Zn(OH)_2$ of a $Zn(OH)_2$-attached ZnS:Ag phosphor (including the case that the attached amount is 0) and the cross contamination with a ZnS:Cu,Al green emitting phosphor component applied before application of the first said phosphor.
Figure 2B:
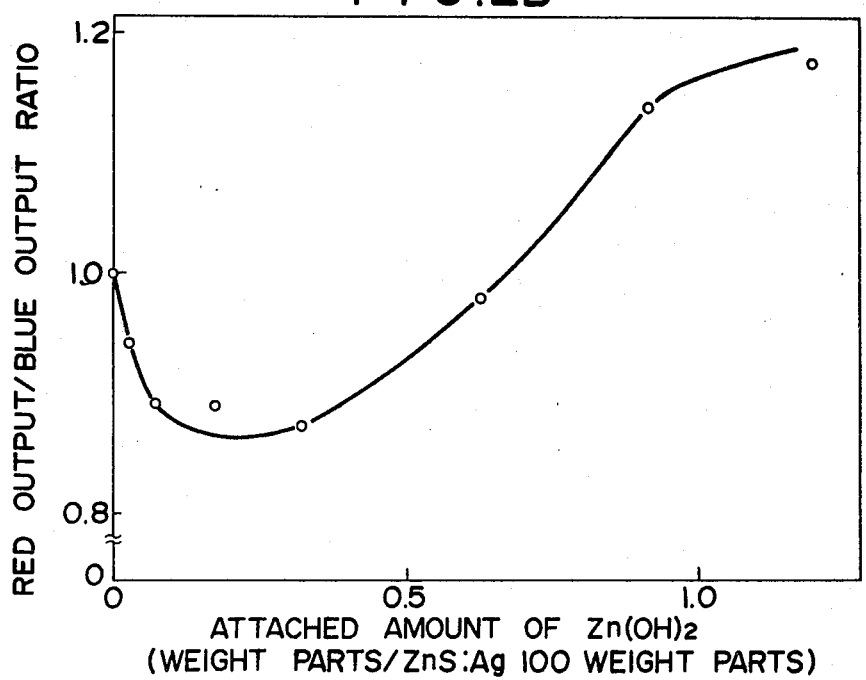
FIG. 2B is a graph showing the relation between the amount of $Zn(OH)_2$ of a $Zn(OH)_2$-attached ZnS:Ag phosphor (including the case that the attached amount is 0) and the cross contamination of a $Y_2O_2S$:Eu red emitting phosphor component applied after application of the above phosphor.

FIG. 2 is a graph showing the relation between the amount of $Zn(OH)_2$ of a $Zn(OH)_2$ attached ZnS:Ag phosphor (including the case that the attached amount is 0) and the cross contamination of the phosphor with other light emitting phosphor components. Two cases of cross contamination are considered cross contamination with a light emitting phosphor component already applied to the face plate (hereinafter, referred to as "cross contamination with a pre-coated light emitting phosphor component") and cross contamination with a light emitting phosphor component which will be applied later (hereinafter, referred to as "cross contamination with a post-coated light emitting phosphor component"). FIG. 2A is a graph showing the relation between the amount of $Zn(OH)_2$ of a $Zn(OH)_2$ attached ZnS:Ag phosphor (including the case that the attached amount is 0) and the cross contamination with a pre-coated ZnS:Cu,Al green emitting phosphor component and the above-described phosphor and FIG. 2B is a graph showing the relation between the amount of $Zn(OH)_2$ of a $Zn(OH)_2$ attached ZnS:Ag phosphor (including the case that the attached amount is 0) and the cross contamination with a post-coated $Y_2O_2S$:Eu red emitting phosphor component and the above-described phosphor. In FIGS. 2A and B, the cross contaminations (plotted on the ordinate) are shown by the values of blue-output/green-output and red-output/blue-output respectively and these values were measured as follows.

Regarding FIG. 2A, after applying the slurry of the phosphor sample on a face plate having thereon stripes of a ZnS:Cu,Al green emitting phosphor component (untreated with $Zn(OH)_2$) formed beforehand and drying, the coated phosphor layer was developed with warm water without performing light exposure. Thereafter (as a matter of course, there was no formation of stripes of a ZnS:Ag phosphor), the stripes of the ZnS:Cu,Al phosphor were excited by ultraviolet ray of 3650 A, the emission thus emitted was divided into two portions by a half mirror, the two lights thus divided were passed through green and blue Wratten filters respectively, and the output of each light was measured by means of a photomultiplier, whereby the value of blue-output/green-output was determined. The value of blue-output/green-output was determined for each phosphor sample and the values were plotted against the amounts of $Zn(OH)_2$ (parts by weight per 100 parts by weight of a ZnS:Ag phosphor) of the phosphor samples, taking the value of the phosphor having no $Zn(OH)_2$ as 1.

Also, regarding FIG. 2B, a phosphor sample was first slurry-coated, exposed, and developed to form stripes of the phosphor on a face plate. Then, a $Y_2O_2S:Eu$ red emitting phosphor component (untreated with $Zn(OH)_2$) was slurry-coated on the face plate having formed thereon the stripes of the phosphor sample, dried, and developed by warm water without being light-exposed. Thereafter (as a matter of course, there was no formation of stripes of the $Y_2O_2S:Eu$ phosphor), the stripes of the phosphor sample were excited by ultraviolet ray of 3650 A, the emission thus emitted was divided into two portions by a half mirror, the two lights thus divided were passed through blue and red Wratten filters respectively, and the output of each light was measured by means of a photomultiplier, whereby the value of red-output/green-output was determined. The value of red-output/green-output was determined on each phosphor sample and the values thus obtained were plotted against the amounts of $Zn(OH)_2$ (parts by weight per 100 parts by weight of the ZnS:Ag phosphor) of the phosphor samples, taking the value of the phosphor having no $Zn(OH)_2$ as 1.

In FIGS. 2A and B, the larger values of blue-output/green-output and red-output/blue-output mean more severe cross contamination of a pre-coated ZnS:Cu,Al phosphor with a ZnS:Ag phosphor and cross contamination of a ZnS:Ag phosphor with a post-coated $Y_2O_2S:Eu$ phosphor.

As is clear from FIG. 2A, the cross contamination with a pre-coated green light emitting phosphor component decreases increasing amount of attached $Zn(OH)_2$. In particular, the reduction in the cross contamination with increase in the amount attached of $Zn(OH)_2$ is remarkable until the amount of $Zn(OH)_2$ is 0.5 part by weight.

Also, as is clear from FIG. 2B, the cross contamination with the post-coated red light emitting phosphor component decreases with increase amount of attached $Zn(OH)_2$ until the amount of $Zn(OH)_2$ is 0.2–0.3 part by weight, but when the amount of $Zn(OH)_2$ further increases, the cross contamination begins to increase and, when the attached amount of $Zn(OH)_2$ is about 0.7 part by weight, the cross contamination is same as that when the amount of $Zn(OH)_2$ is 0. In this invention, the upper limit of the amount of attached $Zn(OH)_2$ is 0.7 part by weight per 100 parts by weight of the phosphor.

As mentioned above, when the amount of attached $Zn(OH)_2$ increases over the upper limit, the cross contamination with a post-coated red light emitting phosphor component increases and one of the reasons for this is considered to be that when the amount of attached $Zn(OH)_2$ increases over a certain value, the dispersibility of the phosphor becomes poor. In more detail, when stripes are formed using a phosphor having degraded dispersibility, the surfaces of the stripes (the surfaces to which postcoating is applied) are liable to become uneven, and this results in cross contamination with the postcoated light emitting phosphor component. The relation between the amount of $Zn(OH)_2$ of a $Zn(OH)_2$ attached ZnS:Ag phosphor (including the case that the attached amount is 0) and the dispersibility of the phosphor is shown in FIG. 3.

Figure 3:
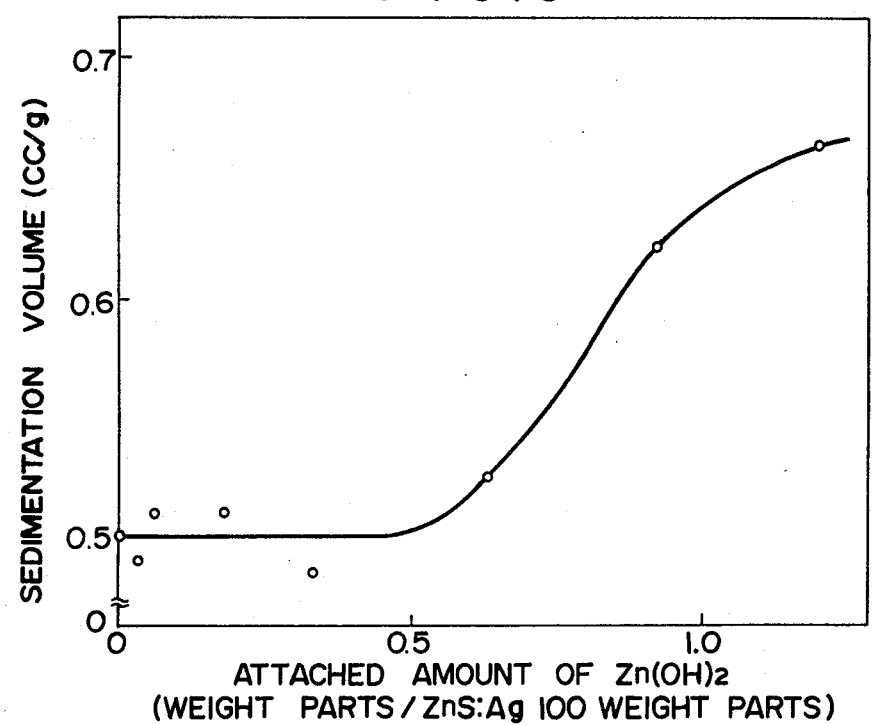
FIG. 3 is a graph showing the relation between the amount of $Zn(OH)_2$ of a $Zn(OH)_2$-attached ZnS:Ag phosphor (including the case that the attached amount is 0) and the dispersibility or sedimentation volume of the phosphor.

In FIG. 3, the dispersibility (plotted on the ordinate) is shown by the sedimentation volume. The sedimentation value is obtained by adding 5 g of a phosphor sample to 30 g of an aqueous polyvinyl alcohol solution containing ammonium bichromate, allowing the mixture to stand for 24 hours in a settling tube, measuring the volume of the sediment, converting the value obtained into volume per gram. A larger sedimentation volume value means poorer dispersibility.

As is clear from FIG. 3, the dispersibility of the phosphor remains almost the same for amounts of attached $Zn(OH)_2$ between and 0.5 part by weight, but when the amount of $Zn(OH)_2$ becomes larger than 0.5 part by weight, the dispersibility becomes worse as the amount of $Zn(OH)_2$ increases. As stated above, the upper limit of the amount of $Zn(OH)_2$ in this invention is 0.7 part by weight per 100 parts by weight of the phosphor from the point of cross contamination with a post-coated light emitting phosphor component. However, considering the dispersibility, it is even more preferable that the amount of $Zn(OH)_2$ be below 0.5 part by weight. In addition, the dispersibility may be improved to some extent by adding a surface active agent to the phosphor slurries and by selecting the surface active agent to be added to the slurries.

The phosphors of this invention greatly increases the light exposure sensitivity of the phosphor slurries.

Figure 4:
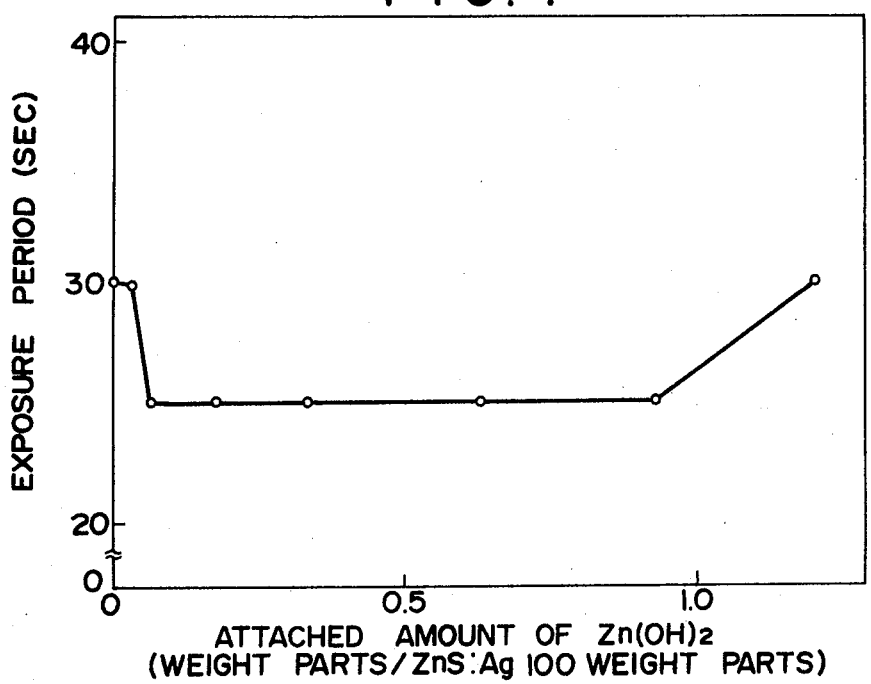
FIG. 4 is a graph showing the relation between the amount of $Zn(OH)_2$ of a $Zn(OH)_2$-attached ZnS:Ag phosphor (including the case that the attached amount is 0) and the light exposure period when stripes of the phosphor having a specific width (230 μm) are formed using the slurry of the phosphor.

FIG. 4 is a graph showing the relation between the amount of $Zn(OH)_2$ of a $Zn(OH)_2$ attached ZnS:Ag phosphor (including the case that the attached amount is 0) and the exposure period necessary for forming stripes of the phosphor having a definite width (230 $\mu$m) using a phosphor slurry of the phosphor. As is clear from FIG. 4, the same stripes are obtained by a shorter exposure period when the amount of attached $Zn(OH)_2$ is between 0 and about 1.2 parts by weight. That is, when the amount of attached $Zn(OH)_2$ is larger than 0 part by weight but not more than about 1.2 parts by weight, the light exposure sensitivity of the phosphor slurries is improved. In particular, when the amount of attached $Zn(OH)_2$ is 0.05–1.0 part by weight, the improvement in the exposure sensitivity is remarkable. Therefore, by using phosphor slurries having thus improved exposure sensitivity, the exposure period can be reduced and the working efficiency can be increased. Furthermore, when the exposure period is the same as that in the case that the attached amount of $Zn(OH)_2$ is 0, the amount of light from a light source for obtaining the same stripes of phosphor can be reduced as compared to the latter case and hence the life of the light source can be prolonged. The reason why the exposure sensitivity of phosphor slurries using phosphor having attached thereto a proper amount of $Zn(OH)_2$ is improved as described above has not yet been clarified but is considered to be that $Zn(OH)_2$ or $Zn^{++}$ formed by a partial dissolution of $Zn(OH)_2$ causes a catalytic action in the phosphorus slurries to promote the photopolymerization of photosensitive resins in the slurries.

The merits or effects of this invention have been described above in respect of the case of using the ZnS:Ag phosphor but it has also been confirmed that the same merits or effects as above are obtained in case of using other phosphors for color television. Moreover, it has also been confirmed that the same merits or effects are obtained in case of using not only phosphors for color television treated by the dispersing agents but also phosphors for color television not treated with the dispersing agents.

As described above, the surface-treated phosphors of this invention for color television can provide phosphor screens for color television picture tubes having remarkably less color mixing. Moreover, when phosphor slurries are prepared using the phosphors, the exposure sensitivity of the phosphor slurries is greatly increased, and thus the industrial utility of the phosphors is very high.

The invention will now be further explained with reference to the following examples.

EXAMPLE 1

In 2 liters of pure water was suspended 1,000 g of a green emitting phosphor component composed of a mixture of a ZnS:Cu,Al phosphor and a ZnS:Au,Al phosphor in a weight ratio of 7:3. To the suspension was added 15 g of water glass, Ooka Seal (trade name, made by Tokyo Ooka K. K., containing 20% by weight $SiO_2$) followed by stirring. 90 g of an aqueous solution of 10% zinc sulfate was further added to the suspension. After stirring the mixture for 10 minutes, the phosphor was allowed to sediment and the supernatant was removed by decantation. Thereafter, the phosphor obtained was washed twice with 5 liters of pure water. Thus, the surface treatment by $SiO_2$ was finished and a phosphor having $SiO_2$ attached thereto was obtained.

The phosphor having attached $SiO_2$ obtained as above was suspended in 2 liters of pure water and 28 g of an aqueous solution of 10% zinc sulfate was added to the suspension. Thereafter the pH of the suspension was adjusted to 10.0 with stirring by the addition of an aqueous NaOH solution. After the pH had been adjusted, the suspension was further stirred for 5 minutes. Thereafter, the phosphor was allowed to sediment and after removal of the supernatant by decantation, the phosphor obtained was washed once with 5 liters of pure water. Then, the phosphor was dehydrated under suction and dried by 3 hours at 150° C. The phosphor thus dried was sieved with a 250 mesh sieve.

The phosphor subjected to the surface treatment by $SiO_2$ and the surface treatment by $Zn(OH)_2$ as described above had $SiO_2$ and $Zn(OH)_2$ attached thereto and in this case, the amount of attached $Zn(OH)_2$ was 0.14 part by weight per 100 parts by weight of the mixed green emitting phosphor component.

A phosphor slurry was then prepared using the phosphor obtained as described above and an ordinary aqueous ammonium bichromate-containing polyvinyl alcohol solution. A coating test was performed using the phosphor slurry thus obtained and the color mixing (haze and cross contamination) and the light exposure sensitivity (exposure time) were determined. The results are shown in Table 1 together with the results of a comparison test wherein a mixed phosphor not subjected to the surface treatment by $Zn(OH)_2$ was used (the figures shown in parentheses in Table 1). The cross contamination (blue output/green output) with a post-coated ZnS:Ag blue emitting phosphor component and the cross contamination (red output/green output) with a post-coated $Y_2O_2S$:Eu red emitting phosphor component were also measured in the case of applying green, blue and red emitting phosphor components successively in this order using the green emitting phosphor component obtained above, a ZnS:Ag phosphor (untreated with $Zn(OH)_2$) as the blue emitting phosphor component, and a $Y_2O_2S$:Eu phosphor (untreated with $Zn(OH)_2$) as the red emitting phosphor component.

As is clear from the results shown in Table 1, the phosphor subjected to the surface treatment with $Zn(OH)_2$ gave less color mixing in the phosphor screen and provided a phosphor slurry having higher exposure sensitivity than was the case when a phosphor which was not subjected to the surface treatment with $Zn(OH)_2$ was used.

EXAMPLE 2

In 2 liters of pure water was suspended 1,000 g of a ZnS:Au,Cu,Al green emitting phosphor component. After addition of 23.6 g of an aqueous solution of 20% zinc chloride to the suspension, the pH of the suspension was adjusted to 8.0 with stirring by the addition of an aqueous $NH_4OH$ solution. After the pH had been adjusted, the suspension was further stirred for 5 minutes. Thereafter, the phosphor was allowed to sediment and after removing the supernatant by decantation, the phosphor obtained was washed twice with 5 liter of pure water. Then, the phosphor was dehydrated under suction and dried for 8 hours at 100° C. The dried phosphor was then sieved with a 250 mesh sieve.

The ZnS:Au,Cu,Al phosphor thus subjected to the surface treatment with $Zn(OH)_2$ had 0.26 part by weight of $Zn(OH)_2$ per 100 parts by weight of the $Zn(OH)_2$ attached thereto.

A phosphor slurry was prepared in the same way as in Example 1 using the phosphor obtained as described above and a coating test was carried out using the phosphor slurry thus obtained to determine the color mixing (haze and cross contamination) and the exposure sensitivity (exposure period of time). The results obtained are shown in Table 1 together with the results of a comparison example wherein ZnS:Au,Cu,Al phosphor not subjected to surface treatment with $Zn(OH)_2$ was used (the figures in parentheses in Table 1). The cross contamination (blue-output/green-output) with a post-coated ZnS:Ag blue emitting phosphor component and the cross contamination (red-output/green-output) with a post-coated $Y_2O_2S$:Eu red emitting phosphor component were measured in the case of coating green, glue and red emitting phosphor components successively in this order using the green emitting phosphor obtained in the above process, a ZnS:Ag phosphor (untreated with $Zn(OH)_2$) as the blue emitting phosphor component, and a $Y_2O_2S$:Eu phosphor (untreated with $Zn(OH)_2$) as the red emitting phosphor component.

As is clear from the results shown in Table 1, the ZnS:Au,Cu,Al phosphor subjected to the surface treatment with $Zn(OH)_2$ gave less color mixing in the phosphor screen and provided phosphor slurries having higher exposure sensitivity than was the case when ZnS:Au,Cu,Al phosphor not subjected to the surface treatment was used.

EXAMPLE 3

In 2 liters of pure water was suspended 1,000 g of a ZnS:Ag blue emitting phosphor component. The suspended phosphor component was surface treated with SiO$_2$ in the manner described in Example 1 to provide phosphor having SiO$_2$ attached thereto.

The phosphor with attached SiO$_2$ obtained was described above was suspended in 2 liters of pure water and after adding 18.7 g of an aqueous solution of 10% zinc acetate to the suspension, the pH of the suspension was adjusted to 9.0 with stirring by the addition of an aqueous NaOH solution. After the pH had been adjusted, the suspension was further stirred for 5 minutes. Thereafter, the phosphor was allowed to sediment and after removal of the supernatant by decantation, the phosphor obtained was washed twice with 5 liters of pure water. Then, the phosphor was dehydrated under suction, dried for 3 hours at 200° C., and then sieved with a 250 mesh sieve.

The ZnS:Ag phosphor subjected to the surface treatment with SiO$_2$ and the surface treatment with Zn(OH)$_2$ as described above had attached thereto 0.08 part by weight of Zn(OH)$_2$ per 100 part by weight of the ZnS:Ag phosphor.

A phosphor slurry was prepared as in Example 1 using the phosphor thus obtained. A coating test was performed using the phosphor slurry obtained and the color mixing (haze and cross contamination) and the light exposure sensitivity (exposure period) were determined. The results are shown in Table 1 together with a comparison example wherein ZnS:Ag phosphor not subjected to the surface treatment with Zn(OH)$_2$ was used (the figures shown in parentheses in Table 1). Cross contamination (blue-output/green-output) with a pre-coated ZnS:Cu,Al green emitting phosphor component and cross contamination (red-output/blue-output) with a post-coated red emitting phosphor component were also determined in the case of applying green, blue, and red emitting phosphor components successively in this order using a ZnS:Cu,Al phosphor (untreated with Zn(OH)$_2$) as the green emitting phosphor component, the blue emitting phosphor obtained as described above, and a Y$_2$O$_2$S:Eu phosphor (untreated with Zn(OH)$_2$) as the red emitting phosphor component.

As is clear from the results shown in Table 1, the ZnS:Ag phosphor subjected to the surface treatment with Zn(OH)$_2$ gave less color mixing in the phosphor screen and provided phosphor slurries having higher exposure sensitivity than was the case when a ZnS:Ag phosphor not subjected to the surface treatment was used.

EXAMPLE 4

In 2 liters of pure water was suspended 1,000 g of a ZnS:Ag,Al blue emitting phosphor component. After addition of 67 g of an aqueous solution of 20% zinc nitrate to the suspension, the pH of the suspension was adjusted to 11.0 with stirring by the addition of an aqueous KOH solution. After the pH had been adjusted, the suspension was further stirred for 5 minutes. Thereafter, the phosphor was allowed to sediment and after removal of the supernatant by decantation, the phosphor obtained was washed once with 5 liters of pure water. Then, the phosphor was dehydrated under suction, dried for 3 hours at 150° C. and sieved with a 250 mesh sieve.

The ZnS:Ag,Al phosphor subjected to the surface treatment with Zn(OH)$_2$ as described above had attached thereto 0.51 part by weight of Zn(OH)$_2$ per 100 parts by weight of the Zn(OH)$_2$ attached ZnS:Ag,Al phosphor.

A phosphor slurry was prepared as in Example 1 using the phosphor obtained as described above and a coating test was performed using the phosphor slurry to determine the color mixing (haze and cross contamination) and the right exposure sensitivity (exposure period). The results are shown in Table 1 together with the results of a comparison example wherein the ZnS:Ag,Al phosphor which was not subjected to the surface treatment with Zn(OH)$_2$ was used (the figures shown in parantheses in Table 1). The cross contamination (blue-output/green-output) with a pre-coated ZnS:Cu,Al green emitting phosphor component and the cross contamination (blue-output/green-output) with a post-coated Y$_2$O$_2$S:Eu red emitting phosphor component were also determined in the case of applying green, blue and red emitting phosphor components using a ZnS:Cu,Al phosphor (untreated with Zn(OH)$_2$) as the green emitting phosphor component, the blue emitting phosphor obtained as described above, and a Y$_2$O$_2$S:Eu phosphor as the red emitting phosphor component.

As is clear from the results shown in Table 1, the ZnS:Ag,Al phosphor subjected to the surface treatment with Zn(OH)$_2$ gave less color mixing in a phosphor screen and provided a phosphor slurry having higher exposure sensitivity than was the case when a ZnS:Ag,Al phosphor not subjected to the surface treatment was used.

EXAMPLE 5

In 2 liters of pure water was suspended 1,000 g of a Y$_2$O$_2$S:Eu red emitting phosphor. Next, 112 g of an aqueous solution of 10% zinc sulfate was added to the suspension, and, the pH of the suspension was adjusted to 9.0 by adding an aqueous NH$_4$OH solution. After the pH value had been adjusted, the suspension was further stirred for 5 minutes. Then, the suspension was allowed to sediment and after removal of the supernatant by decantation, the phosphor obtained was washed thrice with 5 liters of pure water. Then, the phosphor was dehydrated under suction, dried for 6 hours at 130° C., and sieved with a 250 mesh sieve.

The Y$_2$O$_2$S:Eu phosphor subjected to the surface treatment with as described above had attached thereto Zn(OH)$_2$ 0.57 part by weight of Zn(OH)$_2$ per 100 parts by weight of the Zn(OH)$_2$ attached Y$_2$O$_2$S:Eu phosphor.

A phosphor slurry was prepared as in Example 1 using the phosphor obtained as described above and a coating test was performed using the phosphor slurry thus obtained to determine the color mixing (haze and cross contamination) and the light exposure sensitivity (exposure period). The results are shown in Table 1 together with the results of a comparison example wherein Y$_2$O$_2$S:Eu phosphor not subjected to the surface treatment with Zn(OH)$_2$ was used (the figures shown in parentheses in Table 1). The cross contamination (red-output/green-output) with a pre-coated ZnS:Cu,Al green emitting phosphor component and the cross contamination (red-output/blue-output) with a pre-coated ZnS:Ag blue emitting phosphor component were also determined in the case of applying green, blue and red emitting phosphor components using a ZnS:Ag phosphor (untreated with Zn(OH)$_2$) as the blue emitting phosphor component, a ZnS:Cu,Al phosphor (untreated with Zn(OH)$_2$) as the green emitting phosphor component, and the red emitting phosphor obtained as described above.

As is clear from the results shown in Table 1, the Y$_2$O$_2$S:Eu phosphor subjected to the surface treatment with Zn(OH)$_2$ gave less color mixing in a phosphor screen and provided a phosphor slurry having higher exposure sensitivity than was the case when a Y$_2$O$_2$S:Eu phosphor not subjected to the surface treatment was used.

EXAMPLE 6

In 2 liters of pure water was suspended 1,000 g of a red oxide red pigment particle attached Y$_2$O$_2$S:Eu red emitting phosphor. The suspended phosphor was subjected to surface treatment with SiO$_2$ in the manner described in Example 1 to provide SiO$_2$ attached phosphor.

Then, the SiO$_2$ attached phosphor thus obtained was suspended in 2 liters of pure water and 56 g of an aqueous solution of 10% zinc sulfate was added to the suspension. The pH of the suspension was adjusted to 8.0 with stirring by adding an aqueous NaOH solution. After the pH had been adjusted, the suspension was further stirred for 5 minutes. Thereafter, the phosphor was allowed to sediment and the supernatant was removed by decantation. The phosphor was washed twice with 5 liters of pure water. Then, the phosphor was dehydrated under suction, dried for 3 hours at 200° C., and sieved with a 250 mesh sieve.

The red oxide red pigment particle attached Y$_2$O$_2$S:Eu phosphor thus subjected to the surface treatment with SiO$_2$ and the surface treatment with Zn(OH)$_2$ had attached thereto 0.30 part by weight of Zn(OH)$_2$ per 100 parts by weight of the Zn(OH)$_2$ and red oxide red pigment particle attached Y$_2$O$_2$S:Eu phosphor.

Then, a phosphor slurry was prepared as in Example 1 using the phosphor thus obtained and a coating test was performed using the phosphor slurry to determine the color mixing (haze and cross contamination) and the exposure sensitivity (exposure period). The results are shown in Table 1 together with the results in a comparison example wherein a red oxide red pigment particle attached Y$_2$O$_2$S:Eu phosphor not subjected to the surface treatment with Zn(OH)$_2$ was used (the figures shown in parentheses in Table 1). The cross contamination (red-output/green-output) with a pre-coated ZnS:Cu,Al green emitting phosphor component and the cross contamination (red-output/blue-output) with a pre-coated blue emitting phosphor component were determined in the case of applying green, blue and red emitting phosphor components successively in this order using a ZnS:Ag phosphor as the blue emitting phosphor component, a ZnS:Cu,Al green emitting phosphor component as the green emitting phosphor component, and the red emitting phosphor obtained as described above.

As is clear from the results shown in Table 1, the red oxide red pigment particle attached Y$_2$O$_2$S:Eu phosphor subjected to the surface treatment with Zn(OH)$_2$ gave less color mixing in a phosphor screen and provided a phosphor slurry having higher exposure sensitivity than was the case when a red oxide red pigment particle attached Y$_2$O$_2$S:Eu phosphor not subjected to the surface treatment was used.

TABLE 1

| Example | Phosphor | Amount of Zn(OH)$_2$ | Haze (No. of particles) | CROSS CONTAMINATION | | | Exposure period (sec.) |
|---|---|---|---|---|---|---|---|
| | | | | blue output/ green output | red output/ green output | red output/ blue output | |
| 1 | ZnS:Cu,Al + ZnS:Au,Al | 0.14 | 7(74) | 0.90(1.00) | 0.92(1.00) | — | 40(45) |
| 2 | ZnS:Au,Cu,Al | 0.26 | 8(70) | 0.85(1.00) | 0.90(1.00) | — | 40(45) |
| 3 | ZnS:Ag | 0.08 | 8(52) | 0.50(1.00) | — | 0.89(1.00) | 25(30) |
| 4 | ZnS:Ag,Al | 0.51 | 5(50) | 0.30(1.00) | — | 0.95(1.00) | 25(30) |
| 5 | Y$_2$O$_2$S:Eu | 0.57 | 1(13) | — | 0.75(1.00) | 0.70(1.00) | 25(30) |
| 6 | Red oxide red pigment particle attached Y$_2$O$_2$S:Eu | 0.30 | 10(78) | — | 0.45(1.00) | 0.41(1.00) | 35(45) |

*The haze was measured by the method described in connection with FIG. 1, except that the count of the number of remaining particles was performed at five positions and the mean value was used.
*The cross contamination was measured by the method described in connection with FIG. 2 taking the cross contamination when the amount of attached Zn(OH)$_2$ was 0 as 1.
*The exposure period is that necessary for forming stripes of 230μm width as in the case of FIG. 4. A high pressure mercury lamp was used as the light source and the surface illuminance of the face plate was 2000 lux.

What is claimed is:

1. A phosphor comprising a phosphor for color television and zinc hydroxide attached to the phosphor for color television, the amount of said zinc hydroxide being less than 0.7 part by weight per 100 parts by weight of the phosphor for color television.

2. The phosphor as claimed in claim 1 wherein the amount of said zinc hydroxide is 0.01–0.5 part by weight per 100 parts by weight of the phosphor for color television.

3. The phosphor as claimed in claim 1 or 2 wherein the phosphor for color television is a blue emitting phosphor component selected from a silver activated zinc sulfide phosphor, a silver and aluminum activated zinc sulfide phosphor, a cobalt aluminate blue pigment particle attached silver activated zinc sulfide phosphor, and a cobalt aluminate blue pigment particle attached silver and aluminum activated zinc sulfide phosphor.

4. The phosphor as claimed in claim 1 or 2 wherein the phosphor for color television is a green emitting phosphor component selected from a mixed phosphor of a copper and aluminum activated zinc sulfide phosphor and a gold and aluminum activated zinc sulfide phosphor, a copper and aluminum activated zinc sulfide phosphor, a gold, copper and aluminum activated zinc sulfide phosphor, and a copper and aluminum activated zinc-cadmium sulfide phosphor.

5. The phosphor as claimed in claim 1 or 2 wherein the phosphor for color television is a red emitting phosphor component selected from a europium activated yttrium oxisulfide phosphor, a europium activated yttrium oxide phosphor, a red oxide red pigment particle attached europium activated yttrium sulfide phosphor, a red oxide red pigment particle attached europium activated yttrium oxide phosphor, a cadmium sulfoselenide red pigment particle attached europium activated yttrium oxisulfide phosphor, and a cadmium sulfoselenide red pigment particle attached europium activated yttrium oxide phosphor.

6. A phosphor comprising a phosphor for color television and zinc hydroxide and a dispersion agent attached to the phosphor for color television, the amount of said zinc hydroxide being less than 0.7 part by weight per 100 parts by weight of the phosphor for color television.

7. The phosphor as claimed in claim 6 wherein the amount of said zinc hydroxide is 0.01–0.5 part by weight per 100 parts by weight of the phosphor for color television.

8. The phosphor as claimed in claim 6 or 7 wherein the dispersing agent is silicon dioxide.

9. The phosphor as claimed in claim 6 or 7 wherein the phosphor for color television is a blue emitting phosphor component selected from a silver activated zinc sulfide phosphor, a silver and aluminum activated zinc sulfide phosphor, a cobalt aluminate blue pigment particle attached silver activated zinc sulfide phosphor and a cobalt aluminate blue pigment particle attached silver and aluminum activated zinc sulfide phosphor.

10. The phosphor as claimed in claim 6 or 7 wherein the phosphor for color television is a green emitting phosphor component selected from a mixed phosphor of a copper and aluminum activated zinc sulfide phosphor and a gold and aluminum activated zinc sulfide phosphor, a copper and aluminum activated zinc sulfide phosphor, a gold, copper and aluminum activated zinc sulfide phosphor, and copper and aluminum activated zinc-cadmium sulfide phosphor.

11. The phosphor as claimed in claim 6 or 7 wherein the phosphor for color television is a red emitting phosphor component selected from a europium activated yttrium oxisulfide phosphor, a europium activated yttrium oxide phosphor, a red oxide red pigment particle attached europium activated yttrium oxisulfide phosphor, a red oxide red pigment particle attached europium activated yttrium oxide phosphor, a cadmium sulfoselenide red pigment particle attached europium activated yttrium oxisulfide phosphor and a cadmium sulfoselenide red pigment particle attached europium activated yttrium oxide phosphor.

12. The phosphor as claimed in claim 8 wherein the phosphor for color television is a green emitting phosphor component selected from a mixed phosphor of a copper and aluminum activated zinc sulfide phosphor and a gold and aluminum activated zinc sulfide phosphor, a copper and aluminum activated zinc sulfide phosphor, a gold, copper and aluminum activated zinc sulfide phosphor, and copper and aluminum activated zinc-sulfide cadmium phosphor.

13. The phosphor as claimed in claim 8 wherein the phosphor for color television is a red emitting phosphor component selected from a europium activated yttrium oxisulfide phosphor, a europium activated yttrium oxide phosphor, a red oxide red pigment particle attached europium activated yttrium oxisulfide phosphor, a red oxide red pigment particle attached europium activated yttrium oxide phosphor, a cadmium sulfoselenide red pigment particle attached europium activated yttrium oxisulfide phosphor and a cadmium sulfoselenide red pigment particle attached europium activated yttrium oxide phosphor.

* * * * *